(12) United States Patent
Uchida et al.

(10) Patent No.: US 7,076,022 B2
(45) Date of Patent: Jul. 11, 2006

(54) METHOD AND DEVICE FOR X-RAY INSPECTION OF TIRE

(75) Inventors: Norimichi Uchida, Tokyo (JP); Takao Kokubu, Tokyo (JP)

(73) Assignee: Kabushiki Kaisha Bridgestone, Tokyo (JP)

( * ) Notice: Subject to any disclaimer, the term of this patent is extended or adjusted under 35 U.S.C. 154(b) by 0 days.

(21) Appl. No.: 10/509,956

(22) PCT Filed: Apr. 4, 2003

(86) PCT No.: PCT/JP03/04329

§ 371 (c)(1),
(2), (4) Date: Apr. 18, 2005

(87) PCT Pub. No.: WO03/085391

PCT Pub. Date: Oct. 16, 2003

(65) Prior Publication Data

US 2005/0175146 A1    Aug. 11, 2005

(30) Foreign Application Priority Data

Apr. 5, 2002    (JP) .............................. 2002-103263

(51) Int. Cl.
*G01B 15/06* (2006.01)
(52) U.S. Cl. .......................................... 378/61; 378/62
(58) Field of Classification Search ............... 378/57, 378/58, 61, 62
See application file for complete search history.

(56) References Cited

U.S. PATENT DOCUMENTS 4,949,366 A * 8/1990 Collmann .................... 378/61
6,327,333 B1 * 12/2001 Uchida et al. ............... 378/61

FOREIGN PATENT DOCUMENTS

| JP | 53-29790 A | 3/1978 |
| JP | 10-267867 A | 10/1998 |
| JP | 2000-241367 A | 9/2000 |
| JP | 2000-249665 A | 9/2000 |
| JP | 2000-338057 A | 12/2000 |

* cited by examiner

*Primary Examiner*—Courtney Thomas
(74) *Attorney, Agent, or Firm*—Sughrue Mion, PLLC

(57) ABSTRACT

An X-ray tire inspection apparatus comprising X-ray tubes 2a and 2b for applying an X-ray to a tire 10, installed right above the opposite ends of the tire 10 conveyed by a roll conveyor 1, and X-ray line sensors 4a and 4b arranged in the space between adjacent rolls 1R and 1R below the above roll conveyor 1 at positions corresponding to the above X-ray tubes 2a and 2b, respectively, wherein transmission X-ray images of left half and right half portions of the tire 10 are taken by the X-ray line sensors 4a and 4b and combined by tire internal image inspection means 5 to obtain a transmission X-ray composite image of the whole tire 10. Therefore, even a tire having a low aspect ratio can be internally inspected accurately and efficiently.

13 Claims, 8 Drawing Sheets

METHOD AND DEVICE FOR X-RAY INSPECTION OF TIRE

BACKGROUND OF THE INVENTION

1. Field of the Invention

The present invention relates to a method of inspecting the interior of a tire with an X-ray and an apparatus used in the method.

2. Description of the Prior Art

Heretofore, for tire internal inspection, a tire has been taken out from the line, a transmission X-ray image of the tire has been taken by an X-ray camera, and the states of bead wires as tire constituent members and the entry of foreign matter such as a micro-metal or small stone into the tire have been visually checked from the obtained transmission X-ray image of the tire by an operator to judge whether the tire is acceptable or not. In this method in which tires are take out one by one, the production line must be suspended each time inspection is made, thereby reducing productivity. Therefore, the tire internal inspection has to be sampling inspection. In addition, since the work of judging whether a tire is acceptable or not is carried out by operator's visual inspection, the result of judgment is apt to be affected by the skill of each operator and differ by each individual operator.

To cope with these problems, the inventors of the present invention have proposed a method of automating the internal inspection of all the tires in Unexamined Japanese Patent Application No. 2000-249665. As shown in FIGS. 7(a) and 7(b), an X-ray tube 2 and an X-ray generator 3 for driving this X-ray tube 2 are installed at predetermined positions above a roll conveyor 1 for conveying vulcanized tires 10, an X-ray line sensor 4 is arranged in the space between adjacent rolls 1R and 1R below the above roll conveyor 1 at a position corresponding to the X-ray tube 2 to detect an X-ray which has been applied from the above X-ray tube and has passed through the tire 10 conveyed by the roll conveyor 1 in order to take a transmission X-ray image of the above tire continuously, the obtained transmission X-ray image is supplied to the image processing unit 50a of tire internal image inspection means 50 to be processed, and an X-ray image of a normal tire pre-stored in storage means 50b is compared with the above obtained image by a judging unit 50c to judge whether the tire 10 is acceptable or not. This makes it possible to automate the internal inspection of all the tires efficiently without suspending the production line. In the above figures, reference numeral 6 denotes a slit for narrowing the optical path of the applied X-ray, and 7 and 8 denote a lead shield box and a lead curtain installed to prevent an X-ray from leaking from the measurement area to the outside, respectively.

In order to increase the speed and maneuverability by improving the cornering power of a car tire, the tire now tends to have a lower profile. However, in the above method, when a low profile tire such as 205/55 R16 or 215/50 ZR17 is internally inspected, as shown in FIG. 8, the area where images of bead wires 11 and tread belts 12 which are metal members are superimposed becomes large. The portions which become the dead areas of the above metal members are dead areas 11x formed by the bead wires 11 and a dead area 12x formed by the tread belt 12x, all shown in black in the figure and become shadows after image processing. Therefore, even when foreign substances p and q such as metals are existent between the bead wire 11 and the tread belt 12, they cannot be identified and the inspection accuracy is thereby reduced.

Then, as shown in FIG. 9, it is conceivable that the conveyance of the tire 10 is suspended, the tire 10 to be inspected is grasped by a chuck 15, and a transmission X-ray image of the tire is taken while it is turned in order to take a transmission X-ray image of a portion included in the above dead areas 11x and 12x. However, as inspection takes too long in this method, it cannot be said that this method is practical.

It is an object of the present invention which has been made in view of the problems of the prior art to provide an X-ray tire inspection method and apparatus capable of carrying out the internal inspection of even a tire having a low aspect ratio accurately and efficiently.

SUMMARY OF THE INVENTION

The inventors of the present invention have conducted intensive studies and have found that when an X-ray is applied from right above the end portion 10a of a tire as shown in FIG. 10, the dead areas 11x and 12x formed by the belt wires 11 and tread belt 12 become the smallest in half of a transmission X-ray image of the tire 10. The present invention has been accomplished based on this finding.

That is, according to a first aspect of the present invention, there is provided method of inspecting the interior of a tire from a transmission X-ray image of the tire obtained by applying an X-ray to the conveyed tire from X-ray application means, comprising the step of applying the X-ray to at least two positions including the opposite ends of the tires to take transmission X-ray images of the tire. Thereby, an x-ray image having few shadows of the bead wires and the tread belt can be obtained, thereby making it possible to inspect the interior of the tire accurately.

According to a second aspect of the present method, wherein the outer diameter of the conveyed tire is measured and the positions of the X-ray application means are changed according to the measurement result.

According to a third aspect of the present invention, there is provided an X-ray tire inspection method, wherein the X-ray application means are installed a predetermined distance inward from the measurement positions of the outer diameter of the tire.

According to a fourth aspect of the present invention, there is provided an X-ray tire inspection method, wherein two out of the transmission X-ray images of the tire are selected, transmission X-ray images of half portions near the X-ray application means of the tire are combined to form a transmission X-ray composite image of the whole tire, and the interior of the tire is inspected from this transmission X-ray composite image of the whole tire.

According to a fifth aspect of the present invention, there is provided an X-ray tire inspection method comprising the steps of:

measuring the outer diameter of the conveyed tire;

installing the X-ray application means at positions 2 to 3 cm inward from the measurement positions of the outer diameter of the tire based on the measurement data on the outer diameter of the tire;

taking transmission X-ray images of the tire with taking transmission X-ray images of the tire with the X-ray application means;

selecting two out of the transmission X-ray images of the tire to combine the transmission X-ray images of half portions near the X-ray application means of the tire so as to form a transmission X-ray composite image of the whole tire; and inspecting the interior of the tire from the transmission X-ray composite image of the whole tire.

According to a sixth aspect of the present invention, there is provided an X-ray tire inspection apparatus comprising means of conveying tires, means of applying an X-ray to the conveyed tire and X-ray sensors for taking transmission X-ray images of the tire to inspect the interior of the tire from a transmission X-ray image obtained with the X-ray sensors, wherein the X-ray application means are installed at positions corresponding to at least two positions including the opposite ends of the conveyed tire. Thus, by taking transmission X-ray images of the tire from at least two directions by using at least two X-ray application means, an image of the interior of the tire having the smallest dead area can be obtained, thereby making it possible to improve the accuracy of the internal inspection of the tire.

According to a seventh aspect of the present apparatus which further comprises image combining means for selecting two out of the transmission X-ray images of the tire to combine transmission X-ray images of half portions near the X-ray application means of the tire and judging means for judging whether the tire is acceptable or not from a transmission X-ray composite image of the whole tire formed by the image combining means.

According to an eighth aspect of the present invention, there is provided an X-ray tire inspection apparatus which further comprises means of measuring the outer diameter of the conveyed tire and means of moving the X-ray application means to positions a predetermined distance inward from the measurement positions of the outer diameter of the tire.

According to a ninth aspect of the present invention, there is provided an X-ray tier inspection apparatus, wherein the X-ray application means are installed at opposite positions right above the inner wall portion of the tread belt. This is aimed to minimize the influence of the tread belt which has the largest influence upon the dead area.

According to a tenth aspect of the present invention, there is provided an X-ray tire inspection apparatus, wherein one of the X-ray application means and an X-ray sensor for taking a transmission X-ray image of the tire with the X-ray application means are shifted from the other X-ray application means and the other X-ray sensor by a predetermined distance in the tire conveyance distance, respectively. Thereby, since the X-ray application ranges do not overlap with each other, more accurate transmission X-ray images of the tire can be obtained.

According to an eleventh aspect of the present invention, there is provided an X-ray tire inspection apparatus, wherein the X-ray sensors are X-ray line sensors and the X-ray application means are provided with a shielding plate having a slit extending in the internal direction of the tire from the center portion and parallel to the extending direction of the X-ray line sensor. Thereby, the X-ray application ranges can be minimized and the overlapping of the X-ray application ranges of the two X-ray application means can be prevented.

According to a twelfth aspect of the present invention, there is provided an X-ray tire inspection apparatus, wherein the X-ray application means are installed at a height where their X-ray application ranges include at least the whole tire. Thereby, when one of the X-ray application means breaks down, the other X-ray application means is moved above or below the other end of the tire to compensate for this breakdown.

According to a thirteenth aspect of the present invention, there is provided an X-ray tire inspection apparatus, wherein the interval between the two X-ray application means can be changed. Thereby, the internal inspection of various tires which differ in size can be made possible easily.

DETAILED DESCRIPTION OF THE PREFERRED EMBODIMENTS

Preferred embodiments of the present invention will be described hereinbelow with reference to the accompanying drawings.

In the following description, similar parts to those of the prior art are given the same reference symbols.

Figure 1:
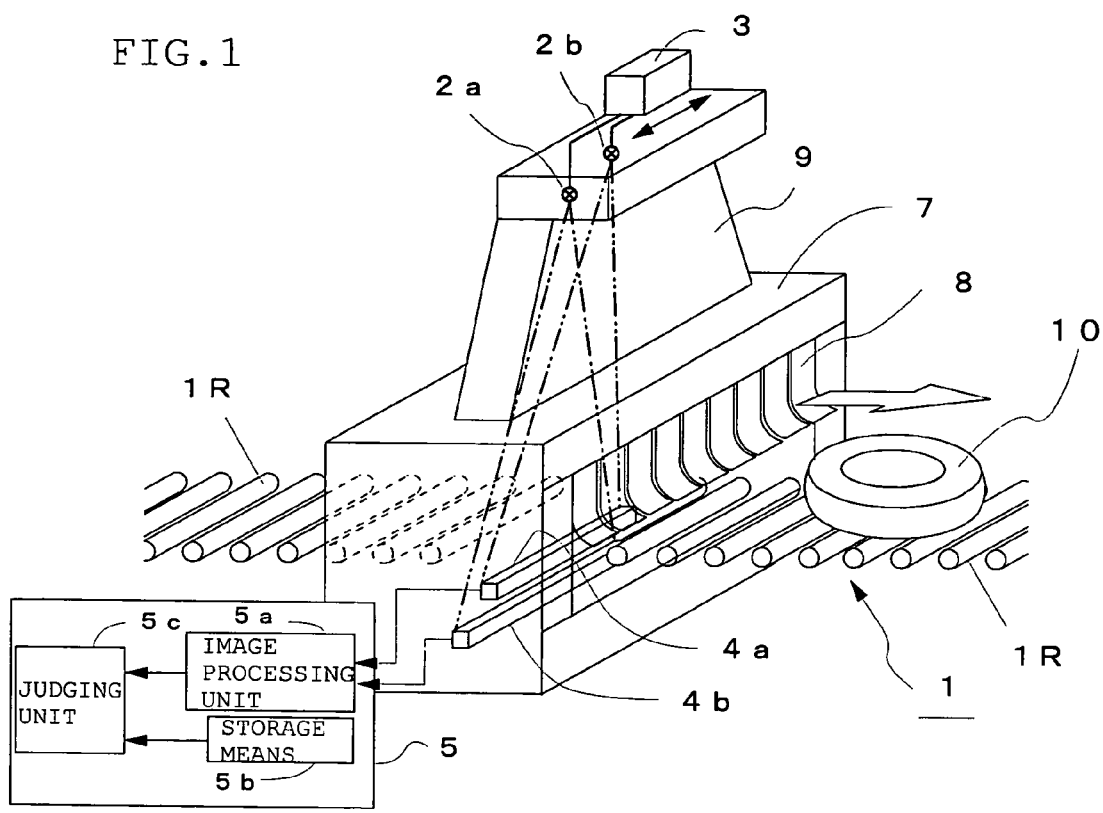
FIG. 1 is a diagram of an X-ray tire inspection apparatus according to an embodiment of the present invention.

FIG. 1 is a diagram of an X-ray tire inspection apparatus according to an embodiment of the present invention. In the figure, reference numeral 1 denotes a roll conveyor for conveying vulcanized tires 10, 7 a lead shield box installed to cover the roll conveyor 1 from above in order to prevent an applied X-ray and reflected X-ray which will be described hereinafter from leaking from the measurement area to the outside, and 8 a lead curtain installed in the passage of the tires 10 in the above lead shield box 7.

2a and 2b represent a pair of X-ray tubes installed at predetermined positions of an X-ray source mounting table 9 mounted on the top of the above lead shield box 7, 3 an X-ray generator for driving the above X-ray tubes 2a and 2b, 4a and 4b X-ray line sensors arranged in the space between adjacent rolls 1R and 1R below the above roll conveyor 1 at positions corresponding to the above X-ray tubes 2a and 2b, respectively, and 5 tire internal image inspection means which comprises an image processing unit 5a for processing a composite image formed by combining transmission X-ray images obtained by the above X-ray line sensors 4a and 4b, storage means 5b for storing an X-ray image of a normal tire, and judging unit 5c for judging whether the tire 10 is acceptable or not by comparing the X-ray image of the normal tire with the obtained image.

Figure 2A:
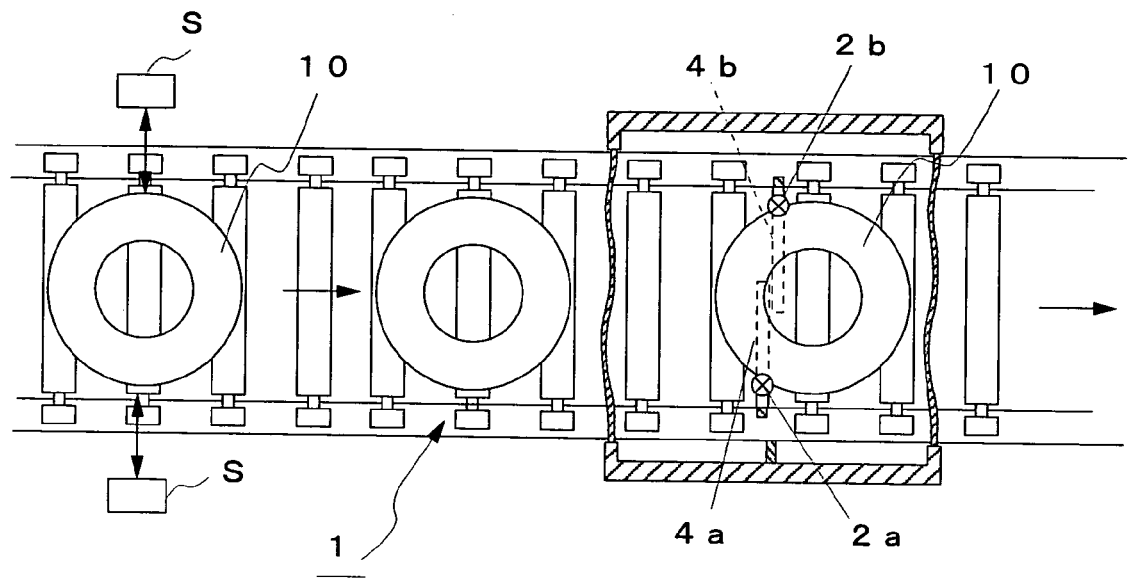
FIGS. 2(a) and 2(b) are diagrams showing the arrangement of X-ray application means according to the embodiment of the present invention.
Figure 2B:
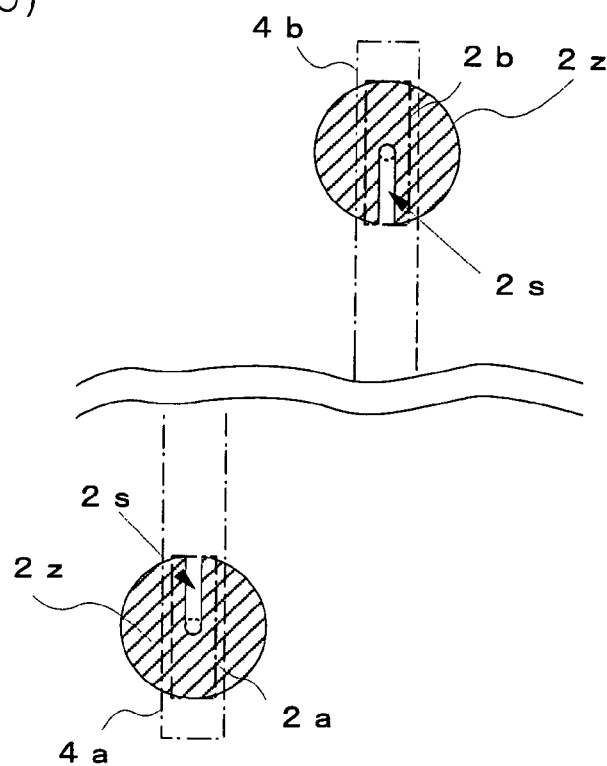

In this embodiment, the relative distance between the above X-ray tubes 2a and 2b can be changed to allow for the internal inspection of various tires which differ in size, and the X-ray tubes 2a and 2b are positioned right above the opposite ends of the tire 10, that is, right above the transit points of the opposite ends of the conveyed tire 10 at the time of measurement. As shown in FIGS. 2(a) and 2(b), the outer diameter of a conveyed tire 10 before inspection is measured by length measuring means such as distance sensors S and S, and the above X-ray tubes 2a and 2b are positioned 2 to 3 cm inward from the outer diameter of the tire. Since these positions are substantially right above the inner wall portion of the tread belt which has the largest influence upon the above dead area, the influence of the tread belt can be minimized.

The X-ray tube 2b is shifted from the other X-ray tube 2a by a predetermined distance in the conveyance direction to prevent the X-ray application ranges of the X-ray tubes 2a and 2b from overlapping with each other, and the X-ray line sensor 4b for taking a transmission X-ray image with the X-ray tube 2b is also shifted from the X-ray line sensor 4a for taking a transmission X-ray image with the X-ray tube 2a by the predetermined distance in the conveyance direction. Thereby, the X-ray application ranges of the above X-ray tubes 2a and 2b do not overlap with each other, whereby a more accurate transmission X-ray image of the tire can be obtained. Further, as the X-ray line sensors 4a and 4b can be prolonged, a transmission X-ray image of the center portion of the tire can be obtained from both of the two X-ray line sensors 4a and 4b. Therefore, a transmission X-ray image of the center portion of the tire is not missing.

In this embodiment, as shown in FIG. 2(b), in order to narrow the optical paths of X-rays applied from the X-ray tubes 2a and 2b down to a predetermined range, the above X-ray tubes 2a and 2b are provided with a shielding plate 2z having a slit 2s extending in the internal direction of the tire 10 from the center portion of an unshown X-ray application window and parallel to the extending direction of the above X-ray line sensors 4a and 4b. Thereby, the X-ray application range can be narrowed down to the minimum and the overlapping of the X-ray application ranges of the above X-ray tubes 2a and 2b can be prevented. Consequently, a clear transmission X-ray image can be obtained.

Figure 3:
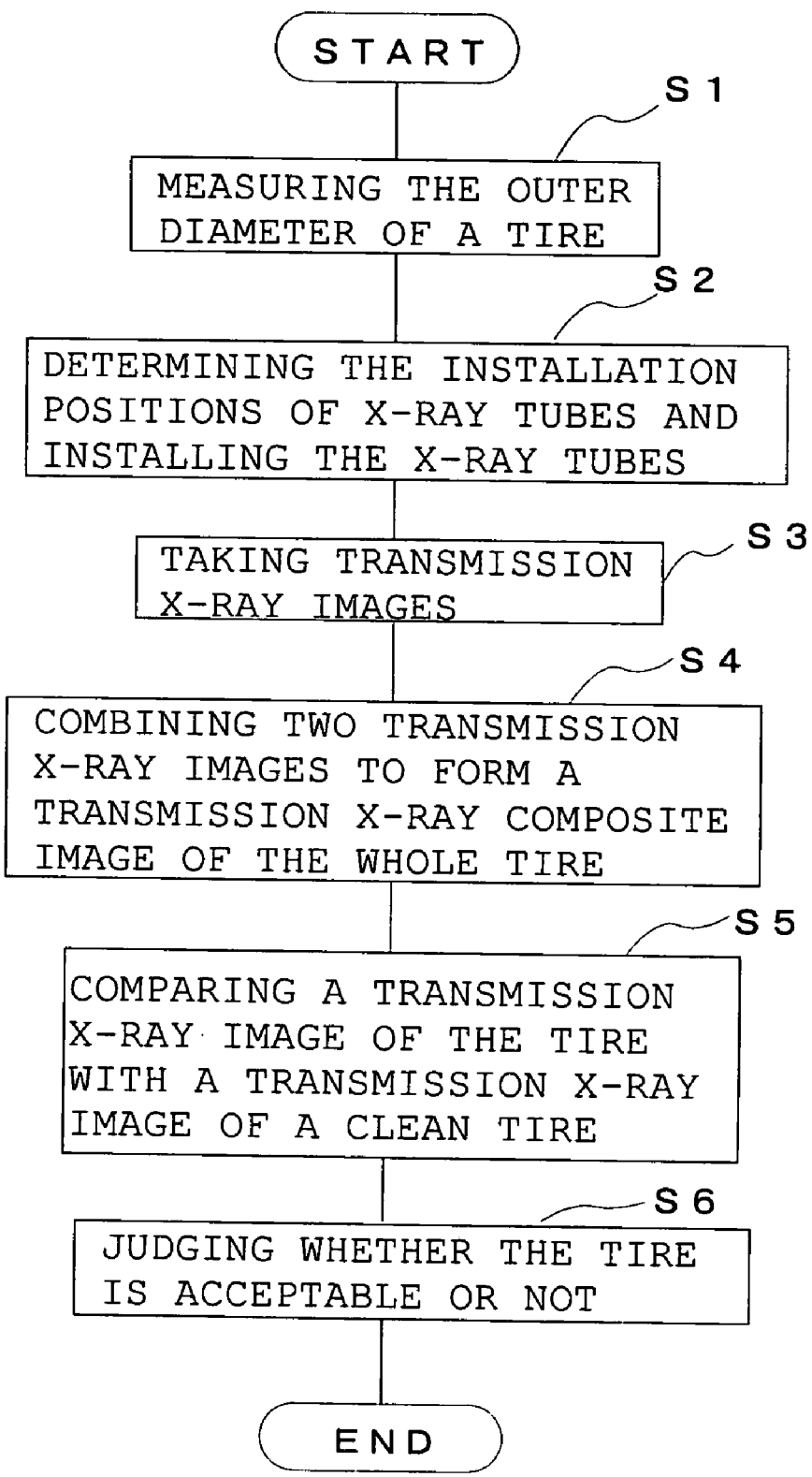
FIG. 3 is a flow chart showing an X-ray tire inspection method according to the embodiment of the present invention.

The X-ray tire inspection method of the present invention will be described hereinbelow with reference to the flow chart of FIG. 3.

Figure 4:
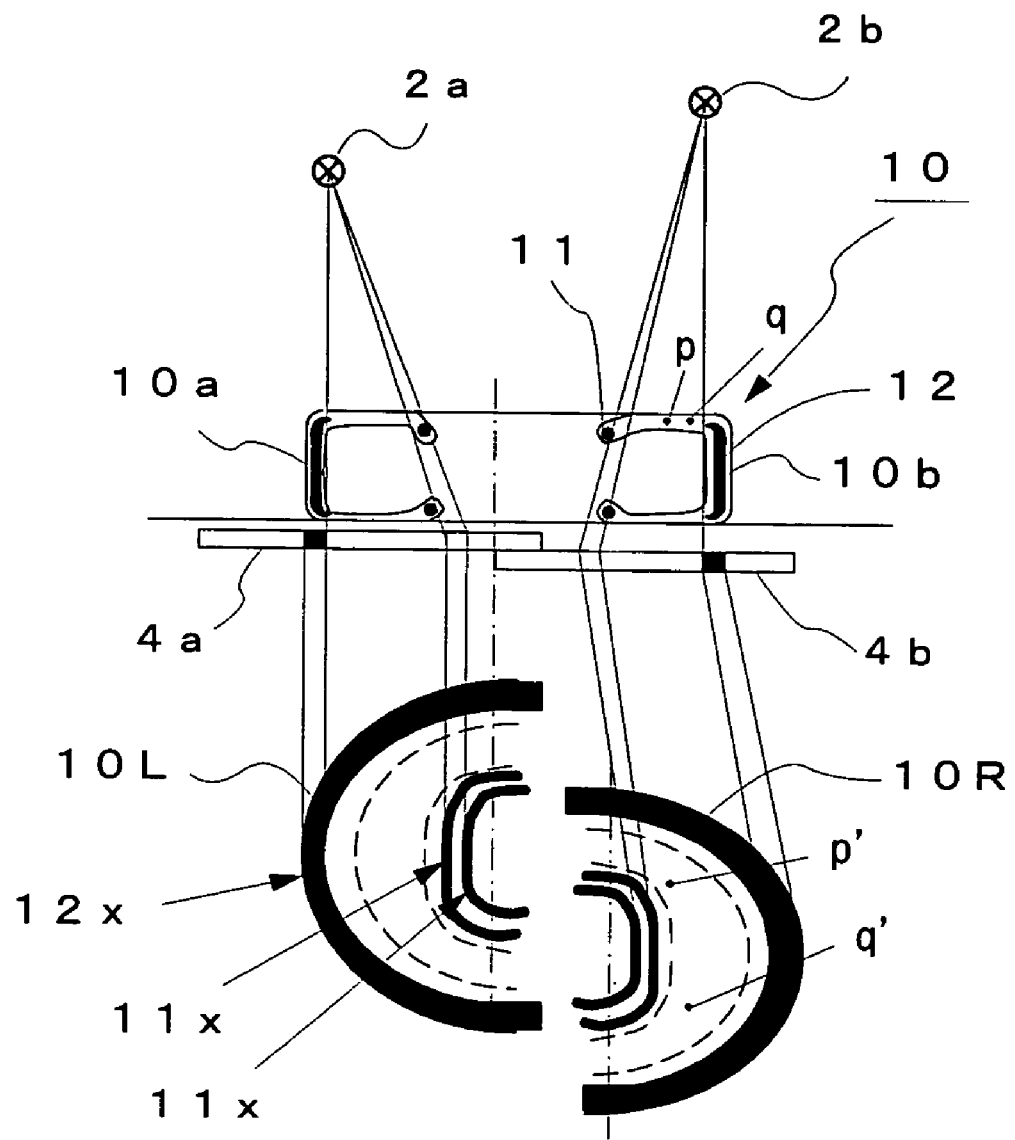
FIG. 4 is a diagram of a transmission X-ray image of the tire according to the embodiment of the present invention.

The outer diameter of the conveyed tire 10 is measured by length measurement means such as distance sensors S and S (step S1), and the above X-ray tubes 2a and 2b are moved almost right above positions 2 to 3 cm inward from the measurement positions of the outer diameter of the tire, that is, almost right above the inner wall portion of the tread belt (step S2). A transmission X-ray image of the tire 10 carried into the lead shielding box 7 which is an inspection site is taken. More specifically, as shown in FIG. 4, an X-ray is applied to the conveyed tire 10 from the X-ray tubes 2a and 2b positioned right above the opposite ends of the tire to take transmission X-ray images 10L and 10R of left half and right half portions of the tire 10 with the X-ray line sensors 4a and 4b, and the obtained transmission X-ray images are supplied to the image processing unit 5a of the tire internal image inspection means 5 (step S3).

The image processing unit 5a combines transmission X-ray images of half portions near the above X-ray tubes 2a and 2b out of the above two transmission X-ray images of the tire to form a transmission X-ray composite image of the whole tire (step S4).

Figure 10:
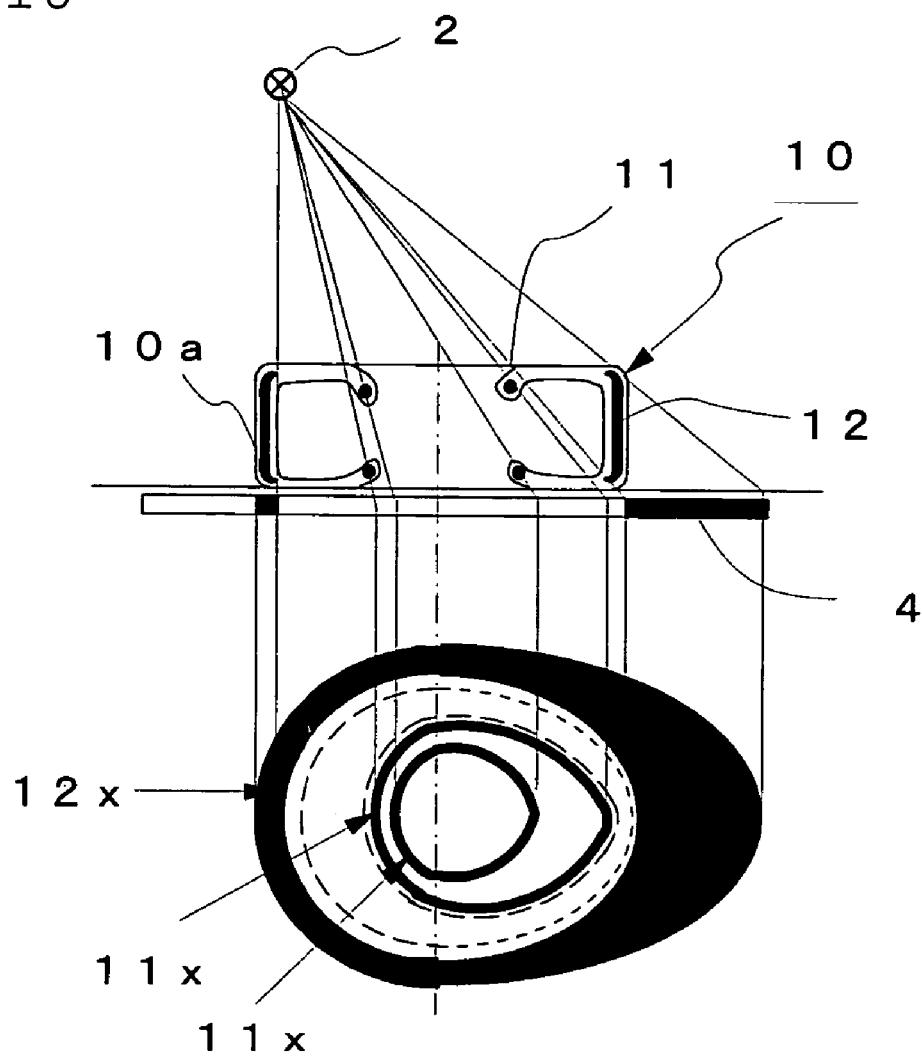
FIG. 10 is a diagram showing the measurement principle of the present invention.

The transmission X-ray images 10L and 10R taken by applying an X-ray from right above the end portions 10a and 10b of the tire have the smallest dead areas 11x and 12x formed by the bead wires 11 and the tread belt 12 as shown in FIG. 10. An image of the interior of the tire which has the smallest dead areas 11x and 12x can be obtained by combining the above transmission X-ray images 10L and 10R.

Finally, the judging unit 5c of the tire internal image inspection means 5 compares the above image of the interior of the tire with an X-ray image of a normal tire pre-stored in the storage means 5b (step S5) to judge whether the tire 10 is acceptable or not by checking if there is foreign matter as large as a predetermined value or more (step S6).

Therefore, as shown in FIG. 4, even when foreign substances p and q such as metals exist between the bead wire 11 and the tread belt 12 of the right half portion of the tire 10, they can be detected from the transmission X-ray image 10R as images p' and q', thereby making it possible to greatly improve the accuracy of the internal inspection (X-ray inspection) of the tire.

Thus, according to this embodiment, since all the tires can be internally inspected automatically and accurately without suspending the production line, the X-ray inspection of the tires can be carried out efficiently. Since the above dead area becomes larger as the tire has a lower profile, the X-ray tire inspection method of the present invention is especially effective for low profile tires.

The storage means 5b of the above tire internal image inspection means 5 may be omitted, the image processing unit 5a may calculate the sizes and number of foreign substances detected from the above tire internal image, and the judging unit 5c may check whether the sizes and number of the above foreign substances satisfy the preset standard values to judge whether the tire 10 is acceptable or not. Alternatively, the above tire internal image inspection means 5 may have only the image processing unit 5a and the above tire internal image may be displayed on a display or the like to enable the operator to judge whether the tire 10 is acceptable or not from the displayed tire internal image.

In the above embodiment, two X-ray tubes 2a and 2b are used to apply an X-ray from above the conveyed tire 10. According to the method of conveying a tire, three or more X-ray tubes may be installed to apply an X-ray to the conveyed tire 10 so as to take transmission X-ray images, thereby obtaining a transmission X-ray image of the whole tire.

In this embodiment, the above X-ray tubes 2a and 2b are installed at a height where their X-ray application ranges include at least the whole tire 10. Thereby, even when one of the X-ray application means breaks down, the other X-ray application means is moved right above the center of the tire 10 to take an image of the whole tire 10. More specifically, when the X-ray application angles of the X-ray tubes 2a and 2b are 34° and the maximum outer diameter of the tire 10 is 80 cm, the above X-ray tubes 2a and 2b are installed at a height of 1.3 m from the sectional position where the outer diameter of the tire becomes largest.

EXAMPLE

Figure 5A:
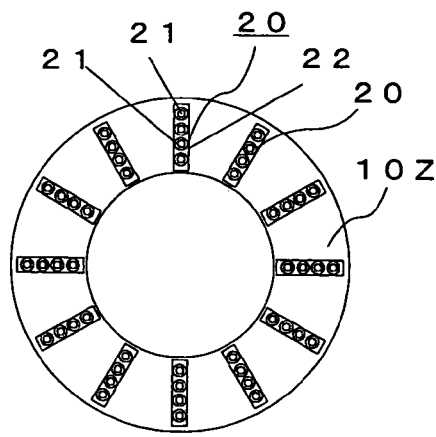
FIGS. 5(a) and 5(b) are diagrams showing a method of evaluating a dead area.
Figure 5B:
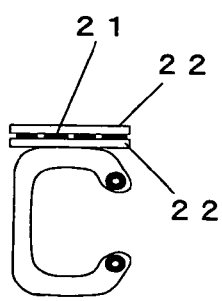
Figure 5B:
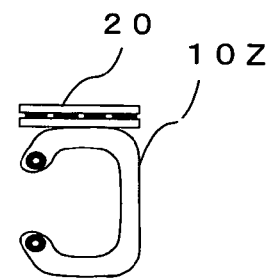
Figure 6A:
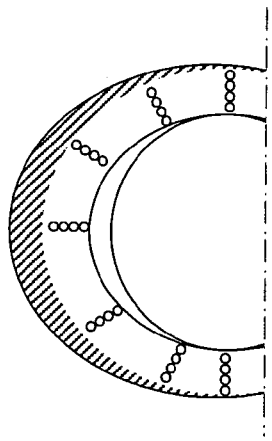
FIGS. 6(a) and 6(b) are diagrams showing the evaluation results of the dead area.
Figure 6B:
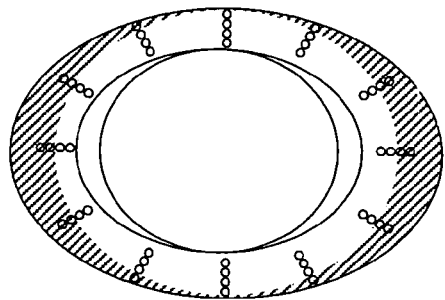
Figure 7A:
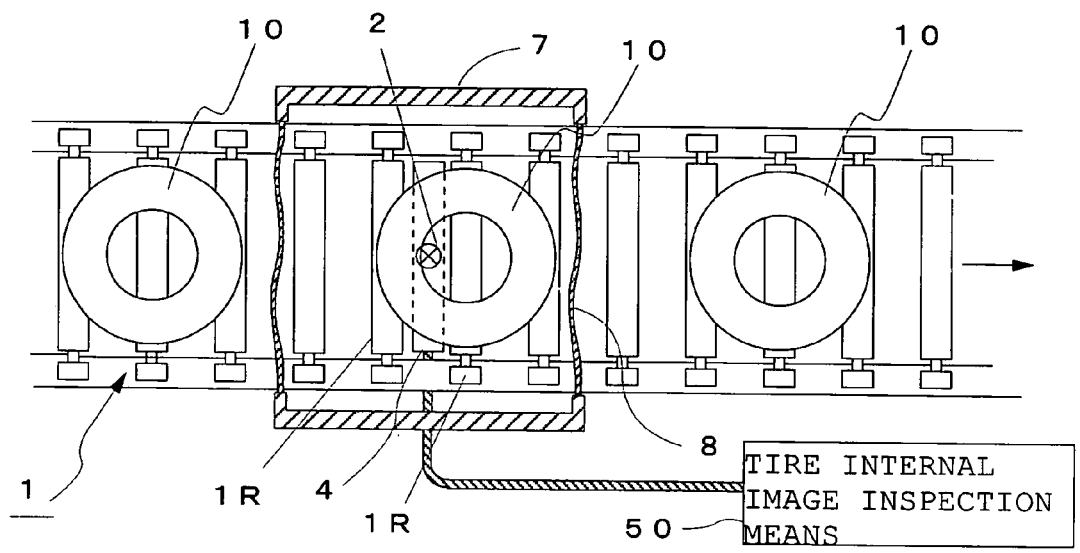
FIGS. 7(a) and 7(b) are diagrams of an X-ray tire inspection apparatus of the prior art.
Figure 7B:
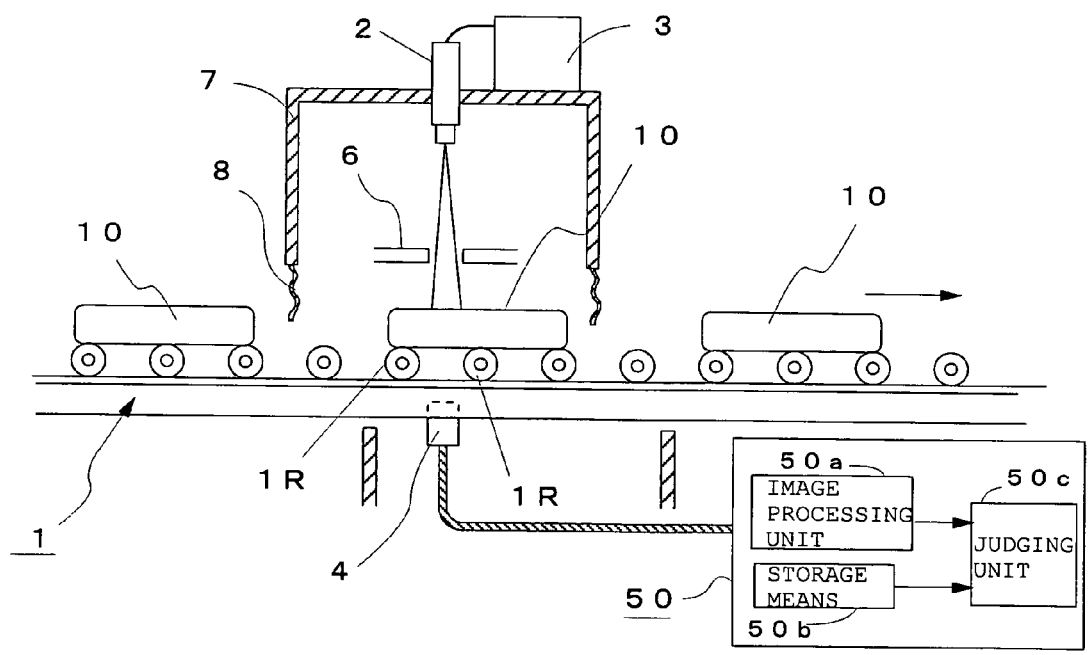
Figure 8:
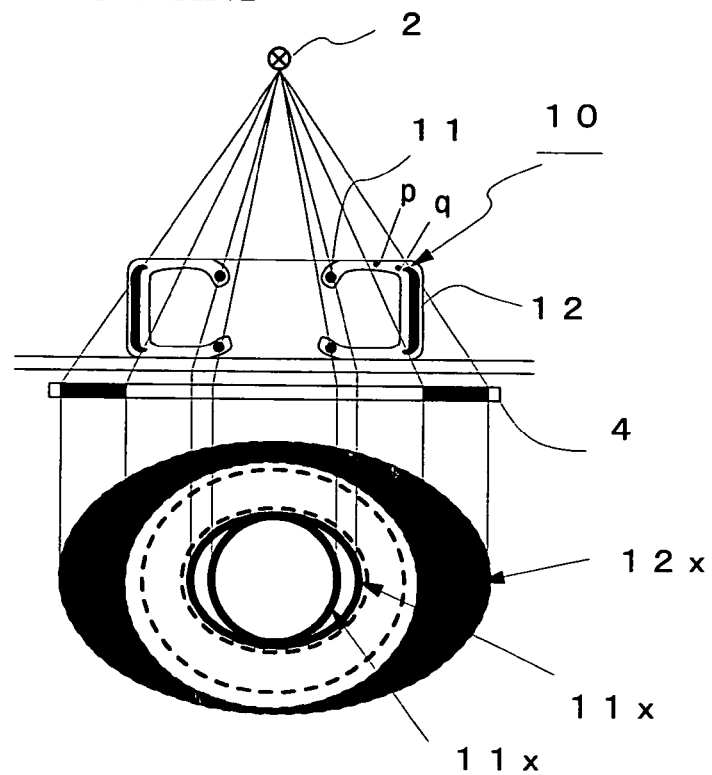
FIG. 8 is a transmission X-ray image of a tire taken by an X-ray inspection apparatus of the prior art.
Figure 9:
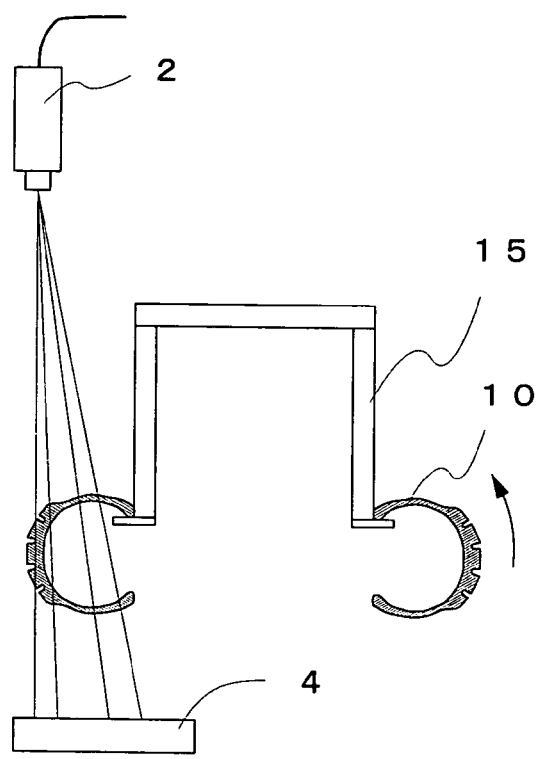
FIG. 9 is a diagram showing another X-ray tire inspection method.

As shown in FIGS. 5(a) and 5(b), 12 test pieces 20 formed by sandwiching four metal washers 21 arranged in a row at equal intervals between two acrylic boards 22 and 22 were arranged symmetrical about the center of a tire 10Z on the side surface of the tire (215/50 ZR17) having an aspect ratio of 50(%) and a transmission X-ray image of this tire 10Z was taken by the X-ray inspection apparatus of the present invention and shown in FIG. 6(a). A transmission X-ray image of the same tire Z taken by an X-ray inspection apparatus having only one X-ray source of the prior art is shown in FIG. 6(b). As obvious from comparison between FIGS. 6(a) and 6(b), since the dead area formed by the tread belt 12 is large in the apparatus of the prior art, only one out of the four washers 21 can be detected. In contrast to this, in the apparatus of the present invention, all the four washers 21 can be detected. Therefore, it is confirmed that the dead area becomes extremely small in the transmission X-ray image of the present invention.

INDUSTRIAL FEASIBILITY

As described above, according to the present invention, when an X-ray is applied to the conveyed tire and the X-ray passing through the above tire is taken by X-ray sensors for the internal inspection of the tire, the above X-ray is applied to at least two positions of the tire as a specimen to take transmission X-ray images of the tire. Therefore, an X-ray image having few shadows of the bead wires and tread belt can be obtained and the interior of the tire can be inspected accurately. Accordingly, the internal inspection of all the tires can be carried out accurately and efficiently without suspending the production line.

What is claimed is:

1. A method of inspecting the interior of a tire from a transmission X-ray image of the tire obtained by applying an X-ray to a conveyed tire from X-ray application means, comprising the step of applying the X-ray to at least two positions including the opposite ends of the tire to take transmission X-ray images of the tire.

2. The X-ray tire inspection method according to claim 1, wherein the outer diameter of the conveyed tire is measured and the positions of the X-ray application means are changed according to the measurement result.

3. The X-ray tire inspection method according to claim 2, wherein the X-ray application means are installed a predetermined distance inward from the measurement positions of the outer diameter of the tire.

4. The X-ray tire inspection method according to any one of claims 1 to 3, wherein two out of the transmission X-ray images of the tire are selected, transmission X-ray images of half portions near the X-ray application means of the tire are combined to form a transmission X-ray composite image of the whole tire, and the interior of the tire is inspected from this transmission X-ray composite image of the whole tire.

5. The X-ray tire inspection method according to claim 1, comprising the steps of:
   measuring the outer diameter of the conveyed tire;
   installing the X-ray application means at positions 2 to 3 cm inward from the measurement positions of the outer diameter of the tire based on the measurement data on the outer diameter of the tire;
   taking transmission X-ray images of the tire with the X-ray application means;
   selecting two out of the transmission X-ray images of the tire to combine the transmission X-ray images of half portions near the X-ray application means of the tire so as to form a transmission X-ray composite image of the whole tire; and
   inspecting the interior of the tire from the transmission X-ray composite image of the whole tire.

6. An X-ray tire inspection apparatus comprising means or conveying tires, means for applying an X-ray to the conveyed tire and X-ray sensors for taking transmission X-ray images of the tire to inspect the interior of the tire from a transmission X-ray image obtained with the X-ray sensors, wherein
   the X-ray application means are installed at positions corresponding to at least two positions of the conveyed tire.

7. The X-ray tire inspection apparatus according to claim 6, which further comprises image combining means for selecting two out of the transmission X-ray images of the tire to combine transmission X-ray images of half portions near the X-ray application means of the tire and judging means for judging whether the tire is acceptable or not from a transmission X-ray composite image of the whole tire formed by the image combining means.

8. The X-ray tire inspection apparatus according to claim 6 or 7, which further comprises means for measuring the outer diameter of the conveyed tire and means for moving the X-ray application means to positions a predetermined distance inward from the measurement positions of the outer diameter of the tire.

9. The X-ray tier inspection apparatus according to claim 6, wherein the X-ray application means are installed at opposite positions right above the inner wall portion of the tread belt.

10. The X-ray tire inspection apparatus according to claim 6, wherein one of the X-ray application means and an X-ray sensor for taking a transmission X-ray image of the tire with the X-ray application means are shifted from the other X-ray application means and the other X-ray sensor by a predetermined distance in the tire conveyance direction, respectively.

11. The X-ray tire inspection apparatus according to claim 6, wherein the X-ray sensors are X-ray line sensors and the X-ray application means are provided with a shielding plate having a slit extending in an internal direction of the tire from a center portion and parallel to an extending direction of the X-ray line sensor.

12. The X-ray tire inspection apparatus according to claim 6, wherein the X-ray application means are installed at a height where their X-ray application ranges include at least the whole tire.

13. The X-ray tire inspection apparatus according to claim 6, wherein an interval between the two X-ray application means can be changed.

* * * * *